United States Patent
Malerba et al.

[11] Patent Number: 6,083,204
[45] Date of Patent: Jul. 4, 2000

[54] METHOD AND APPARATUS FOR GRAVITY-FED INTRAVENOUS INFUSION

[76] Inventors: Richard Malerba, 11 Beecher St., Coram, N.Y. 11727; Alan Binder, 11 Vaux Hall Ct., Melville, N.Y. 11747

[21] Appl. No.: 09/162,790

[22] Filed: Sep. 29, 1998

[51] Int. Cl.[7] .................................................. A61M 5/00

[52] U.S. Cl. ....................... 604/181; 604/212; 604/246; 604/257

[58] Field of Search .................................. 604/181, 187, 604/199, 212–214, 218, 222, 226, 246, 247, 257

[56] References Cited

U.S. PATENT DOCUMENTS

| | | | |
|---|---|---|---|
| 937,029 | 10/1909 | Strong | 604/214 |
| 2,950,717 | 8/1960 | Bouet | 604/214 |
| 3,166,070 | 1/1965 | Everett | 604/214 |

*Primary Examiner*—Wynn Wood Coggins
*Assistant Examiner*—Deborah Blyveis
*Attorney, Agent, or Firm*—Eliot S. Gerber

[57] ABSTRACT

A fluid is injected for a period of 2 to 30 minutes using an intravenous injection ("IV") system which includes a syringe. The syringe includes an internal bag, which receives fluid, a plunger and a finger-operated air valve. The syringe operates by ambient air pressure and does not require hand-pushing or motor operation.

16 Claims, 5 Drawing Sheets

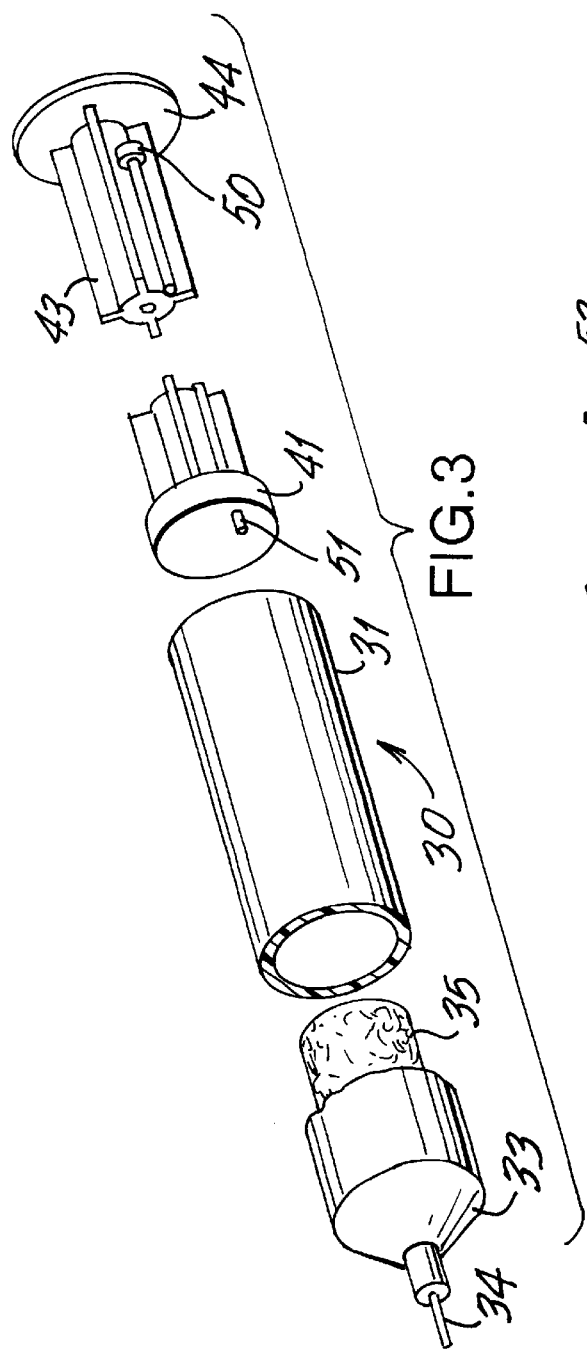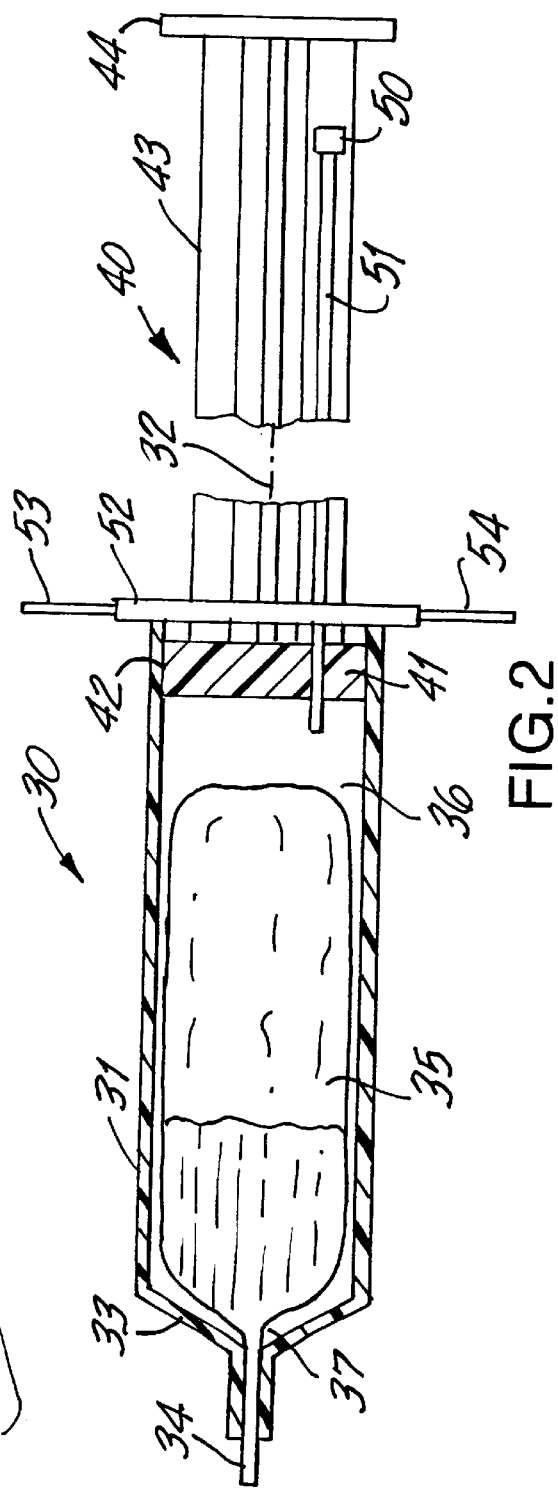

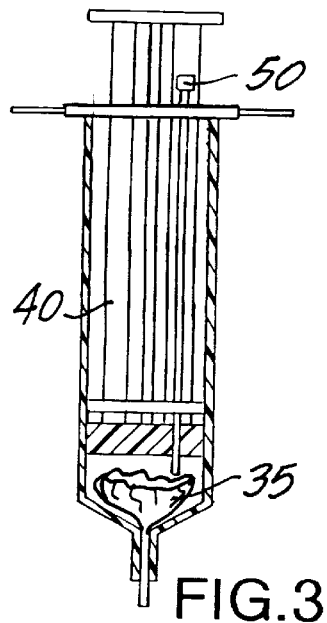
FIG.3A
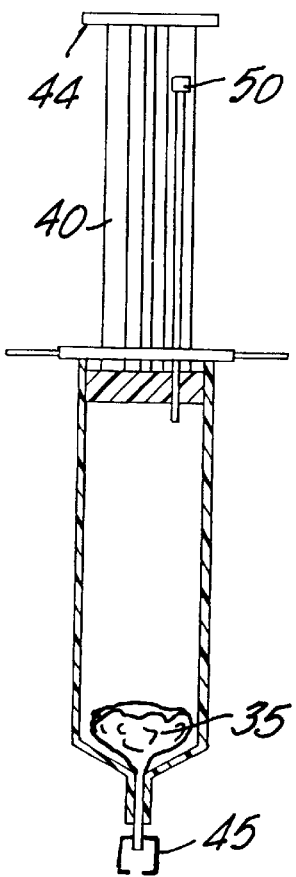
FIG.3B
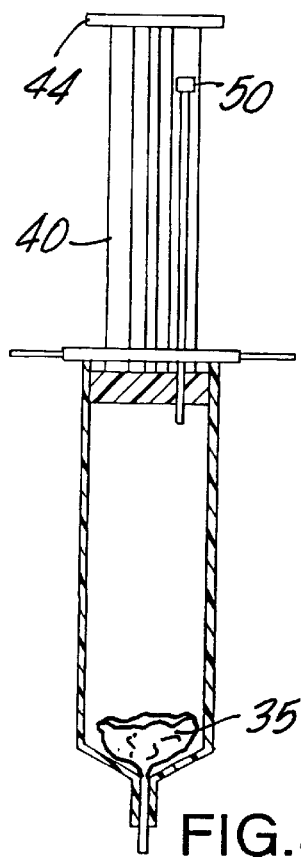
FIG.3A1
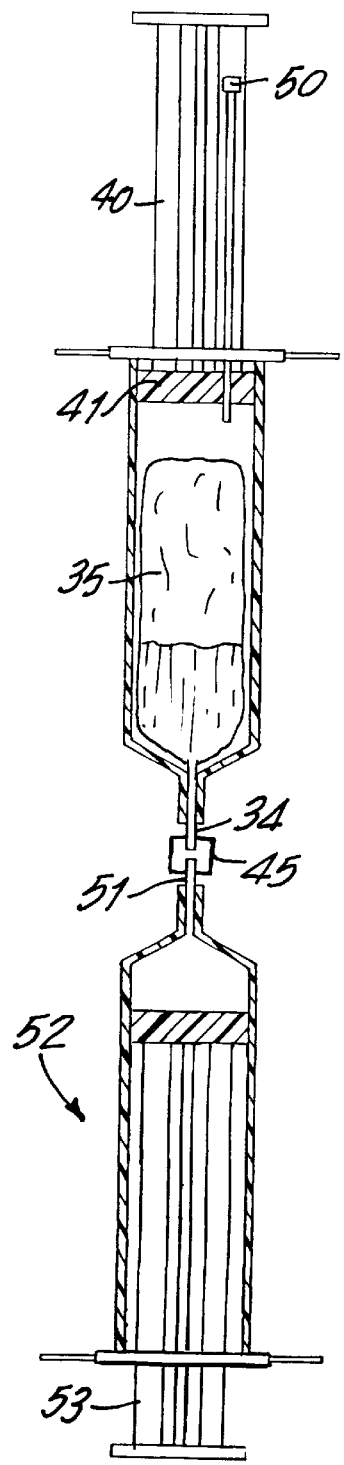
FIG.3C

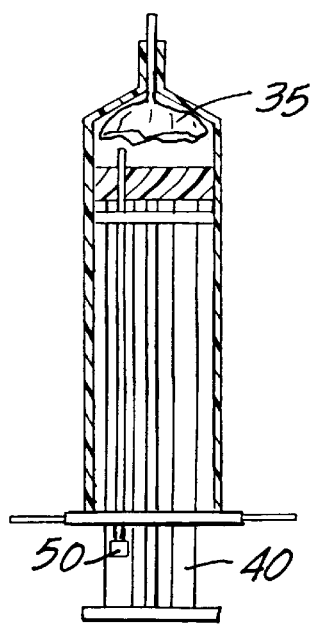
FIG.4A
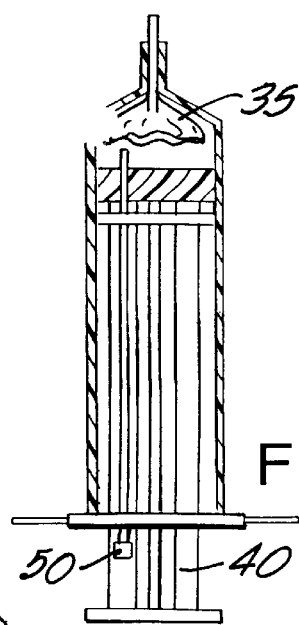
FIG.4B
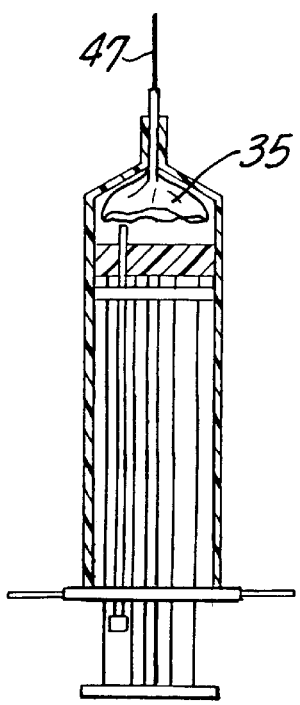
FIG.4C
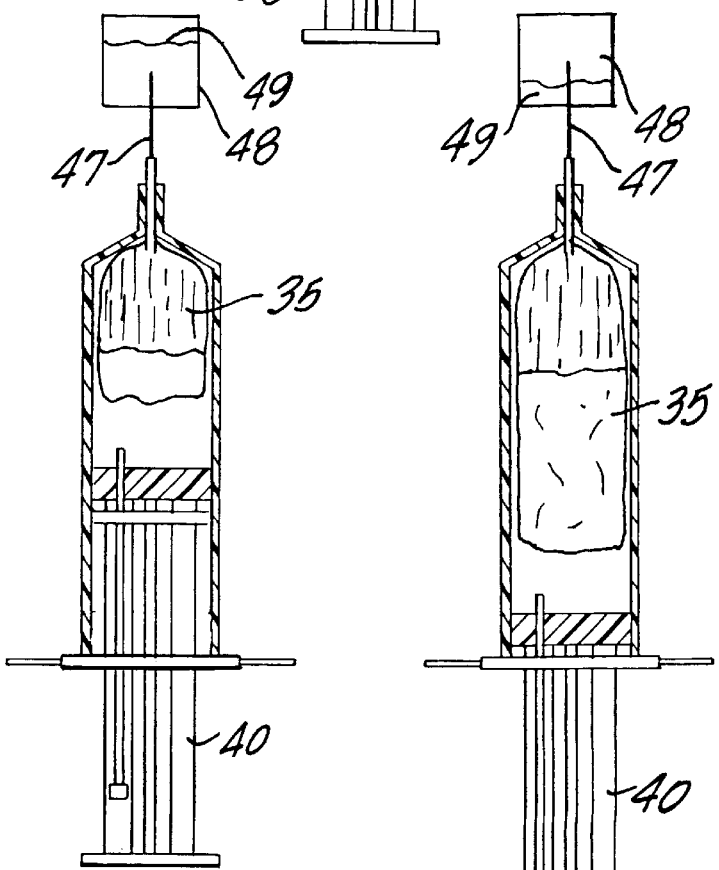
FIG.4D
FIG.4E

METHOD AND APPARATUS FOR GRAVITY-FED INTRAVENOUS INFUSION

FIELD OF THE INVENTION

The present invention relates to medical devices and more particularly to intravenous gravity-fed drip injection devices.

BACKGROUND OF THE INVENTION

At the present time there are a number of medical procedures which call for a prolonged period of injecting a liquid into a patient's veins, i.e., intravenous injection ("IV"). For example, an antibiotic drug in liquid form, or other "piggyback" fluids, may be injected for a period of 2 to 30 minutes, most often 10–15 minutes.

A number of devices have been suggested and are commercially available for such so-called "drip IV". The most commonly used device is a hand-operated (hand delivered) IV push syringe device. It requires a nurse, or other healthcare professional, to push on a plunger for 2–20 minutes. That device requires the attention of an operator. It is labor-intensive and suitable personnel may not always be available when they are needed for such hand-delivered IV medication. In addition, the operator is not always able to push on the device with a constant pressure, for example, due to inattention or fatigue. Since the operator's hand pressure is not constant, the delivery of the drug is also uneven, which is generally undesirable. Another device is a motor driven precision infusion pump. However, such pumps are expensive, may require specially trained personnel, and may not be suitable for home use.

U.S. Pat. No. 5,476,449 shows a syringe for injecting fluids using an intravenous (IV) infusion tube having a connector. A syringe plunger is slidably disposed in the syringe.

In U.S. Pat. No. 4,245,655 entitled "Blood Collection Device" a syringe has the distal end of a plunger received in its chamber and a collection bag made of flexible material. When the plunger is withdrawn it causes a vacuum around the bag so that the bag fills with blood and expands.

U.S. Pat. No. 5,032,117 discloses a syringe for the gravity-feeding of IV drugs. The syringe is suspended above the patient. A needle penetrates a stopper to vent the interior to ambient air.

SUMMARY OF THE INVENTION

In accordance with the present invention there is provided an intravenous (IV) infusion device to inject a liquid, such as a piggyback liquid antibiotic, into a patient. It delivers the liquid in a constant (even) stream over a selected period, for example, 10–15 minutes. The device of the present invention operates by ambient air pressure. It does not require hand-pushing, or other constant operator attention, so its functioning does not depend on the ability or attentiveness of an operator. It frees the nurse, or other health care professional, from this time-consuming task. It does not require a precision electric pump or electronic controls or a spring-driven mechanism so that, compared to such devices, it is relatively inexpensive and reliable. It does not rely, for its push force, on the elasticity of a rubber bag or other elastomeric material, as such materials may lose elasticity or may not apply a constant force.

The present gravity IV device isolates the liquid from the ambient air so the liquid remains sterile and without airborne contamination. It is a closed system. It is an inexpensive and disposable (one-time use) device, so there is no danger of contamination due to re-use or improper sterilization.

The present IV device does not require a secondary administration set to deliver fluid, which is a significant cost saving. It is attached directly to the main IV line, unlike the device of U.S. Pat. No. 5,032,117 which requires a secondary administration set.

The device comprises a large syringe having a plunger which slides in the syringe barrel with an air-tight seal. The plunger, when it is withdrawn, creates a partial vacuum within the barrel. The syringe has a nozzle having a connector adapter to be connected to an IV line. A flexible non-elastomeric bag, preferably of medical grade flexible plastic film, is positioned within the barrel and has its orifice sealed to the barrel above the nozzle or sealed to a tube through the nozzle, or secured to the internal wall of the barrel by a gasket. A finger-operable variable air valve leads to the interior of the barrel (barrel cavity) and controls ambient air flow into the barrel.

In one method of operation, the nozzle is connected to a needle which is inserted into a supply of the liquid to be administered to the patient. The air valve is first opened, the plunger is depressed so that the plunger is down, and the bag is collapsed. The operator then closes the air valve and pulls the plunger up (withdrawn) drawing liquid into the bag by negative pressure. With the plunger withdrawn and the bag filled, the needle is removed, the nozzle is attached to the IV line, and the device is suspended above the patient. The operator then opens the air valve. The ambient air pressure will enter the barrel, causing the bag to slowly deflate and causing the liquid to flow out through the center of the nozzle and IV line, with the control of flow being controlled by a fixed open valve. That valve may be positioned in the nozzle or line to control liquid flow and/or prevent too rapid flowing of the liquid. That valve, for example, may be a needleless drop orifice sized to deliver 1, 2 or 3 cc/min.

In an alternative method of using the device, fluid is forced (pumped) into the bag, for example, from another syringe. In this method the air valve is opened, the plunger is drawn back, allowing maximum fill space, a supply syringe is connected to the nozzle, the plunger of the supply syringe is operated forcing its liquid into the bag, the supply syringe is removed and the air valve is closed. A control valve is connected to the device and it is hung above the patient, i.e., attached to the IV line near an appropriate Y port using the catcher arm lock. Then the Y port is assessed (the nozzle is connected to the Y port), the air valve is opened, air enters the barrel and the liquid flows out of the bag by gravity.

In either of these two methods the IV crimping mechanism, within the arm lock of the device, can be used to stop flow in the main IV line. If the crimping mechanism is used, it will prevent mixing of the main line solution with the device solution.

BRIEF DESCRIPTION OF THE DRAWINGS

The following detailed description should be considered in conjunction with the accompanying drawings. In the drawings:

FIG. 2 is an enlarged side cross-sectional view of the device of FIG. 1 with the plunger in its raised (withdrawn) position;

FIG. 3 is an exploded view of the syringe of the present invention;

FIGS. 3A–3C are side cross-sectional views of the device of FIG. 1 illustrating the first method using the device;

FIGS. 4A–4E are side cross-sectional views of the device of FIG. 1 illustrating a second method of using the device;

FIGS. 5A, 5B and 5C are side cross-sectional views of alternative constructions for the proximal end of the syringe in which FIG. 5C shows the most preferred embodiment.

DETAILED DESCRIPTION OF THE INVENTION

Figure 1:
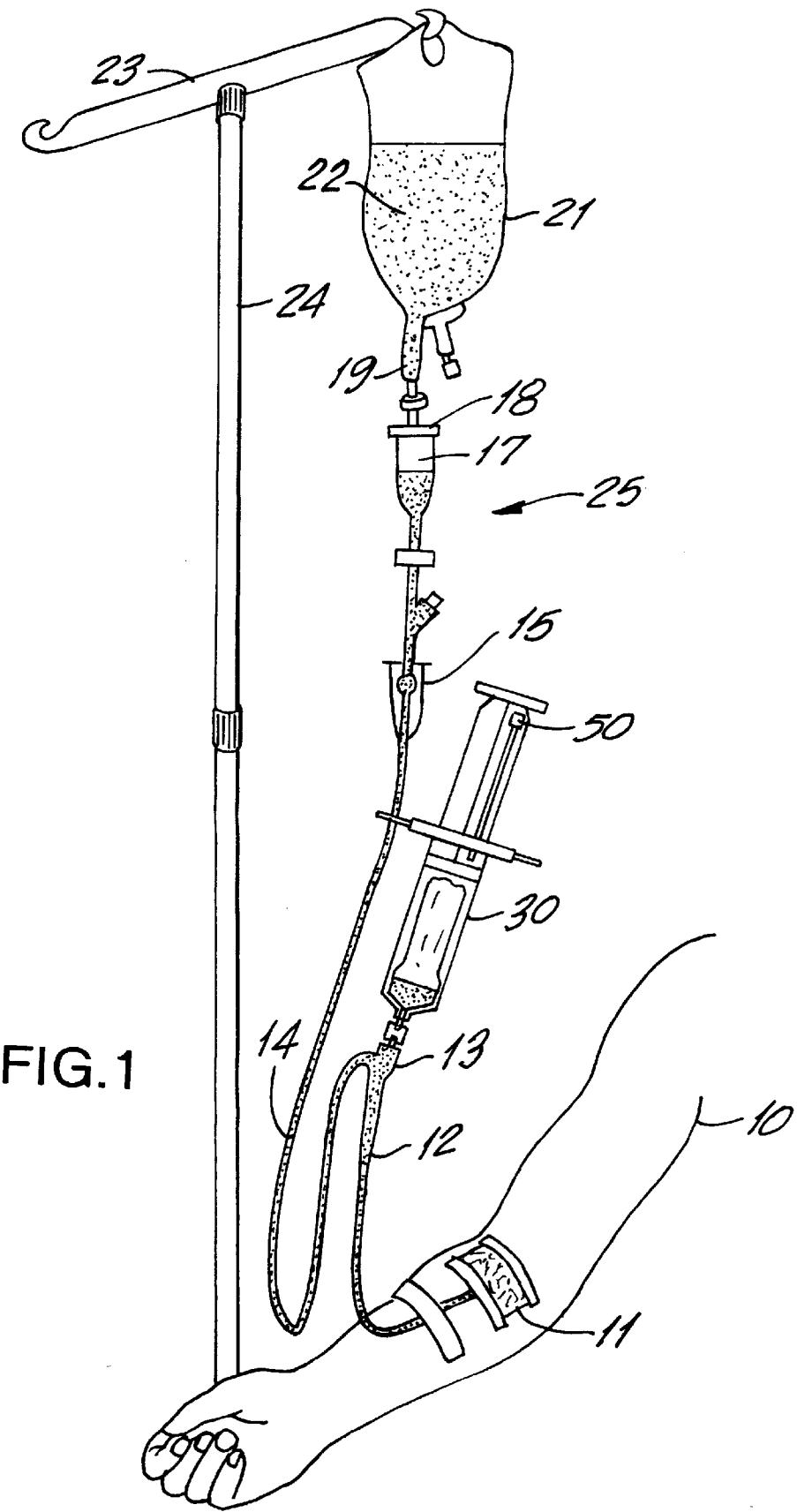
FIG. 1 is a side view showing the IV infusion device of the present invention as used on a patient.

As shown in FIG. 1, which illustrates the first method of using the device, the present invention is of methods and apparatus for gravity-fed intravenous (IV) infusion. A needle (not shown) pierces a vein in the patient's arm 10 and an exposed portion of the needle is held under bandage 11. The needle, at its exposed proximal end, has a connector (not shown) which may be under bandage 11 and which is connected to IV line (tube) 12. The line 12 leads to a Y branch having a connector 13 which is a device access port. The line 12 has loop 14 and leads to a holder device and open-close valve 15 and a closed-top funnel 17. The top 18 of funnel 17 has a line (tube) 19 which is inserted into, or otherwise connected to, an integral bottom tube leading from supply bag 21. The supply bag 21 is filled with fluid 22 and the bag 21 is hung on arm 23 of a stand 24. The bag 21 is hung so that it is above the patient's arm 10. These lines and devices are, so far, conventional and commercially widely available portions of an IV system 25.

However, the system 25 also includes the syringe 30 of the present invention. The syringe 30 includes a connector which fits into connector 13.

As shown in FIG. 2, the syringe 30 includes a cylindrical barrel 31 which is a round ring in cross-sections perpendicular to an imaginary axis. The barrel is preferably of a strong transparent plastic. The barrel is about 3 cm in diameter. The bottom of the barrel 31 is closed by cap portion 33 which is integral with, or joined to, the barrel. The cap portion has a tube 34 which extends beyond the cap 33 and is adapted to tightly fit in a line connector 13.

Figure 5A:
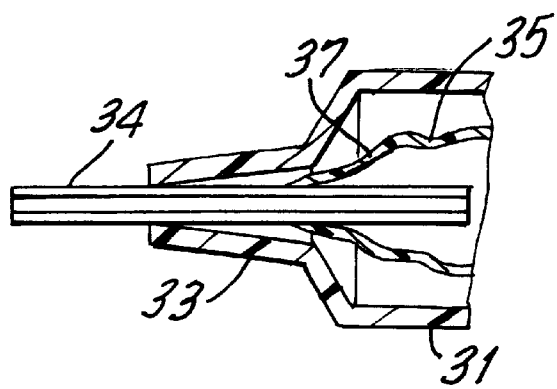

A bag 35 is positioned within the cavity 36 of the barrel 31. The bag is preferably of a non-elastomeric plastic film. The bag will become unfurled (unwrinkled) when filled with liquid but will not expand, as it is not elastic. The bag 35, at its lower end, terminates in tube portion 37 which is sealed onto the portion of tube 34 which is within the cavity 36. A liquid may pass through tube 34 to fill bag 35 and bag 35 is emptied when liquid within it flows out through tube 34, see FIG. 5A.

Figure 5B:
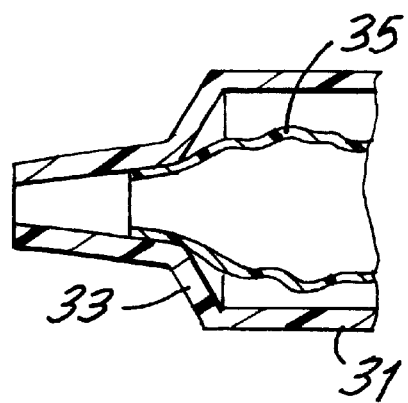
Figure 5C:
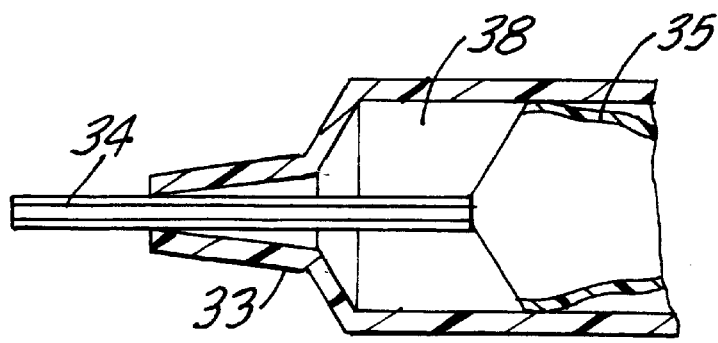

In FIG. 5B the bag 35 is sealed to the inside of cap portion 33, which is an alternative to tube 34. The most preferred embodiment is shown in FIG. 5C in which a rubber gasket 38 is in the form of a disk having a hole therethrough for the tube 34. The gasket 38 is within the bag 35 and seals the bag against the internal wall of the barrel, e.g., it expands to squeeze the bag against the barrel wall.

As shown in FIG. 2, plunger 40 having a plunger head 41 slides within the barrel 31. The plunger head 41 which is disk-like in cross-section perpendicular to axis 32 and has a rim 42 forming an air-tight seal with the inner wall of the barrel 31. The head 41 is fixed to shaft 43 at the shaft's distal end, and the shaft 43 is fixed to disk-like handle 44 at its proximal end. The shaft is a stiff plate in the form of a cross (cross-sections perpendicular to axis 32), but alternatively it may be of other shapes. An air intake valve 50, having opened and closed positions, is located on the top of stiff air tube 51. The tube 51 extends through a hole in head 41 so that its distal orifice opens into the cavity 36. The tube 51 is fixed to the shaft 43 and moves with it.

Figure 6:
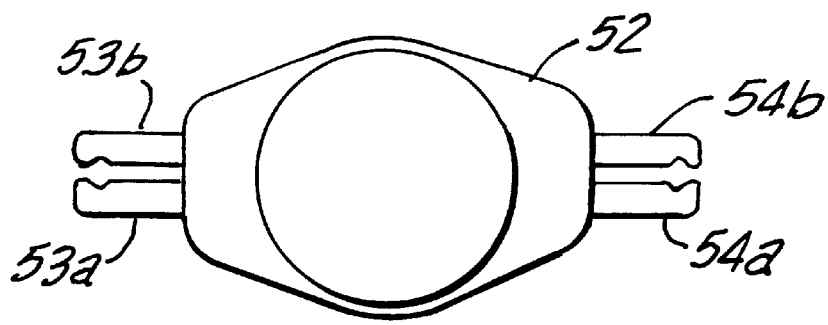
FIG. 6 is a top view of the catcher arm lock mechanism on the syringe which fits on the IV line and the IV line crimping mechanism.

A plate 52 has opposite pairs of arms 53a, 53b and 54a, 54b (see FIG. 6) which are catcher arm locks used to attach the syringe 30 to an IV line. In addition, an IV line placed between the arms 53a and 53b (or 54a and 54b) would be closed due to pressure from those arms, see FIG. 6.

In the method shown in FIGS. 3A–3C, in the first step the air intake valve 50 is opened, generally by the fingers of the nurse or other health-care professional. The bag 35 is in its unfilled and collapsed state and the plunger 40 is manually lifted allowing adequate air space in the barrel for expansion of the bag 35, see FIG. 3A1.

The next step, shown in FIG. 3B, is to join the tube 34 (nozzle of the syringe) to a coupling adapter 45.

FIG. 3C illustrates the next step in which coupling adapter 45 is coupled to the nozzle 51 of a second syringe 52. Then the plunger 53 of the second syringe 52 is depressed, forcing liquid 54 out through nozzle 51, through coupling adapter 45 and tube 34 and into bag 35. Then the valve 50 is closed and the coupling adapter 45 removed from the tube 34. The syringe 30 has been filled with the liquid, i.e., the drug, and is ready to be used. The liquid has not come into contact with air and is therefore unlikely to become contaminated.

FIGS. 4A–4E illustrate the second method of the present invention. In FIG. 4A, the air valve 50 is opened, the plunger 40 is depressed and the bag 35 is empty and collapsed. The valve 50 is open. Then, in FIG. 4B the valve 50 is closed.

In FIG. 4C a tubular needle 47 is connected in the exposed portion of tube 34. In FIG. 4D the needle is injected through the wall of a container 48 having a supply of liquid 49. The point of the needle extends into the liquid 49. The plunger 40 is partly withdrawn and starts filling the bag 35 with the liquid 49. In FIG. 4E the plunger 40 is fully withdrawn and the bag 35 is filled. Subsequently, and not shown, the needle 47 is withdrawn from container 48 and the needle 47 is removed from tube 34. The device is then ready to be used to infuse the liquid within the bag 35 into a vein of a patient, as shown in FIG. 1.

The device must be hung vertically and above the arm of the patient. Excess IV tubing must be looped, as shown in FIG. 1, for the proper flow of fluid.

I claim:

1. A syringe for the gravity feeding of a liquid to a patient by constant and prolonged intravenous (IV) infusion from the force of ambient air pressure; the syringe comprising:

(a) a barrel having a cover portion;

(b) a nozzle;

(c) a plunger comprising a plunger head, the plunger head fitting air-tightly within the barrel and sliding therein, and a plunger handle which extends beyond the barrel and is adapted to be pulled and pushed by hand; a barrel cavity being formed between the cover head and the plunger portion which varies in size as the plunger is pushed;

(d) a non-elastomeric flexible liquid-tight bag positioned within the barrel between the plunger head and the barrel cover portion, the bag having a portion which is sealed proximate the cover portion to permit liquid to flow through the nozzle and into the bag, the bag being adapted to be compressed by ambient air pressure and not by the plunger head; and (e) an air valve means in communication with the cavity for permitting ambient air flow into the barrel cavity when the air valve is opened and air flow out of the barrel when the plunger is pushed to reduce the size of the barrel cavity, the air valve means including a two-way finger-operated air valve.

2. A syringe as in claim 1 wherein the barrel has a cylindrical body portion comprising a uniform circular ring in cross-section taken perpendicular to an imaginary axis of the barrel and the body portion has an inner tubular wall.

3. A syringe as in claim 2 wherein the plunger head is a round disk-like member having a circumferential edge and having an air-tight seal on its circumferential edge which bears against the inner wall of the barrel.

4. A syringe as in claim 2 wherein the nozzle includes a tube having a portion extending into the bag.

5. A syringe as in claim 2 wherein the nozzle is a tube having a portion extending beyond the cover portion outside of the barrel.

6. A syringe as in claim 2 wherein the plunger also comprises a shaft portion connecting the handle and the plunger head.

7. A syringe as in claim 1 and an air tube which extends through the plunger head to the cavity and having a top portion between the handle and the plunger head, the air valve means being positioned proximate the top portion of the air tube to control air flow through the air tube.

8. A syringe as in claim 2 wherein the flexible bag is formed of a flexible sheet of plastic film.

9. A syringe for IV infusing of a patient over a period of about 2–30 minutes, the syringe comprising:

(a) a barrel having a tubular body portion and a cover portion;

(b) a nozzle means to flow liquid into and out of the barrel body portion;

(c) plunger means including a plunger head to slide within the barrel by hand pressure and thereby apply air pressure within the barrel, the plunger head having sealing means to prevent air leakage and the plunger means having handle means to push and pull the plunger head;

(d) bag means to contain liquid, the bag means comprising a flexible plastic liquid-tight non-elastomeric bag positioned in a cavity formed between the plunger head and the barrel cover portion, the bag being adapted to be compressed by ambient air and not by the plunger head;

(e) means to connect the bag means to the nozzle means to permit liquid to flow through the nozzle and into and out of the bag means; and (f) air valve means, including a finger-operated two-way valve, to control air flow into and out of the cavity, the control of air flow into the cavity being over the period of 2–30 minutes to compress the bag with ambient air.

10. A syringe as in claim 9 wherein the body portion is a uniform circular ring in cross-section taken perpendicular to an imaginary axis of the barrel and having an inner tubular wall.

11. A syringe as in claim 10 wherein the plunger head is a round disk-like member having a circumferential edge and having an air-tight seal on its circumferential edge which bears against an inner wall of the barrel.

12. A syringe as in claim 10 wherein the nozzle means comprises a tube having a portion extending into the cavity.

13. A syringe as in claim 9 wherein the nozzle means comprises a tube having a portion thereof extending beyond the cover portion and outside of the barrel.

14. A syringe as in claim 9 wherein the plunger means also comprises a shaft connecting the handle means and the plunger head.

15. A syringe as in claim 9 and an air tube which extends through the plunger head to the cavity and having a top portion between the handle and the plunger head, the air valve means being positioned proximate the top portion of the air tube.

16. A syringe as in claim 1 and including a catcher arm lock means to attach the syringe to an IV line.

* * * * *